United States Patent [19]

Reichenberger

[11] Patent Number: 4,697,588

[45] Date of Patent: Oct. 6, 1987

[54] SHOCK WAVE TUBE FOR THE FRAGMENTATION OF CONCREMENTS

[75] Inventor: Helmut Reichenberger, Eckental, Fed. Rep. of Germany

[73] Assignee: Siemens Aktiengesellschaft, Berlin and Munich, Fed. Rep. of Germany

[21] Appl. No.: 807,894

[22] Filed: Dec. 11, 1985

[30] Foreign Application Priority Data

Dec. 27, 1984 [DE] Fed. Rep. of Germany ....... 3447440

[51] Int. Cl.⁴ ............ A61B 17/22

[52] U.S. Cl. ............ 128/328

[58] Field of Search ............. 128/328, 24 A; 367/163, 367/174, 175, 156, 168; 181/400, 401, 167, 168, 0.5, 142; 179/181 R, 115 R, 115.5 R, 115.5 ES, 115.5 PV, 115.5 VC; 340/384, 385, 388

[56] References Cited

U.S. PATENT DOCUMENTS

| | | | |
|---|---|---|---|
| 1,730,531 | 10/1929 | Robbins | 179/181 R X |
| 4,526,168 | 7/1985 | Hassler et al. | 128/328 X |

FOREIGN PATENT DOCUMENTS

| | | | |
|---|---|---|---|
| 0081051 | 6/1983 | European Pat. Off. . | |
| 760163 | 5/1953 | Fed. Rep. of Germany . | |
| 1191720 | 4/1965 | Fed. Rep. of Germany . | |
| 2436856 | 2/1975 | Fed. Rep. of Germany . | |
| 3146628 | 6/1983 | Fed. Rep. of Germany | 128/328 |
| 3312014 | 10/1984 | Fed. Rep. of Germany . | |
| 528145 | 11/1921 | France . | |

*Primary Examiner*—Michael H. Thaler
*Attorney, Agent, or Firm*—Mark H. Jay

[57] ABSTRACT

In a shock wave tube for concrement fragmentation in a patient the coil is formed as a plane flat coil. A tubular connecton leads from the region between the flat coil and a diaphragm disposed before it to the suction side of a vacuum pump. During operation of the shock wave tube, the diaphragm is sucked against the flat coil. The arrangement has the advantage that a pressure chamber for pressing the diaphragm from the outside is eliminated. Therefore the shock waves need not pass through any exit windows, owing to which malfunctions due to cracks in the exit window are obviated. The shock wave tube can be designed in a very compact form in conjunction with reflectors. The reflectors preferably have a parabolic form with a focus at which the concrement of the patient is positioned.

26 Claims, 7 Drawing Figures

SHOCK WAVE TUBE FOR THE FRAGMENTATION OF CONCREMENTS

BACKGROUND OF THE INVENTION

The invention relates to a shock wave tube with a coil to which a diaphragm is adjacent. The invention relates in particular to a shock wave tube which is used for concrement fragmentation in medical therapy.

Shock wave tubes of this kind have been known for some time and can, according to recent studies as described e.g. in German Offenlegungsschrift No. 33 12 014, be employed in medical practice for the fragmentation of concrements in the body of a patient. There a shock wave tube is described. The shock wave tube has a covered coil, so that the emitted shock wave converges to a focus. In front of the coil, an insulating foil and a metal diaphragm are arranged. To obtain an effective shock wave, the diaphragm must closely abut the coil. To this end, a cavity filled with a pressurized liquid is placed in front of the diaphragm.

It has been found that those materials which are under the pressure necessary for urging the diaphragm towards the coil are under especially strong stress exerted by the passing shock wave due to the resulting continuous prestress. With ordinary emission windows (e.g. of plexiglass) for the shock wave, it was found that after the passage of several shock waves this compressive prestress may lead to cracking. The positive pressure can then no longer be maintained.

One object of the invention is to develop a shock wave tube that is not destroyed in this fashion. In accordance with the invention, this is achieved because the shock wave do not pass through any parts subjected to a continuous pressure difference, other than the diaphragm.

According to the invention, the diaphragm is sucked against the coil with negative pressure relative to its surroundings.

An advantage of the invention is that a positive pressure for pressing the diaphragm against the coil is eliminated. This obviates also the chamber needed for maintaining the positive pressure and the layer of material provided in this chamber as an exit window, which is traversed by the shock wave. Through the elimination of this layer there results as a further advantage: no interaction with this layer can take place. Such interaction adversely affects the amplitude as well as the timing and geometry of the shock wave.

In a preferred embodiment, the coil is designed as a planar flat coil, and a tubular connection is provided. One end of the connection lies in the region between the diaphragm and the flat coil, its other end being connectable to the suction side of a vacuum pump provided for creating the negative pressure.

Due to the negative pressure between the flat coil and the diaphragm, even the diaphragm's edge region abuts the flat coil. Upon triggering of the shock wave, the diaphragm is abruptly deflected from its resting position; thereafter it is quickly damped by the back-suction force, and returns rapidly to its original position.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
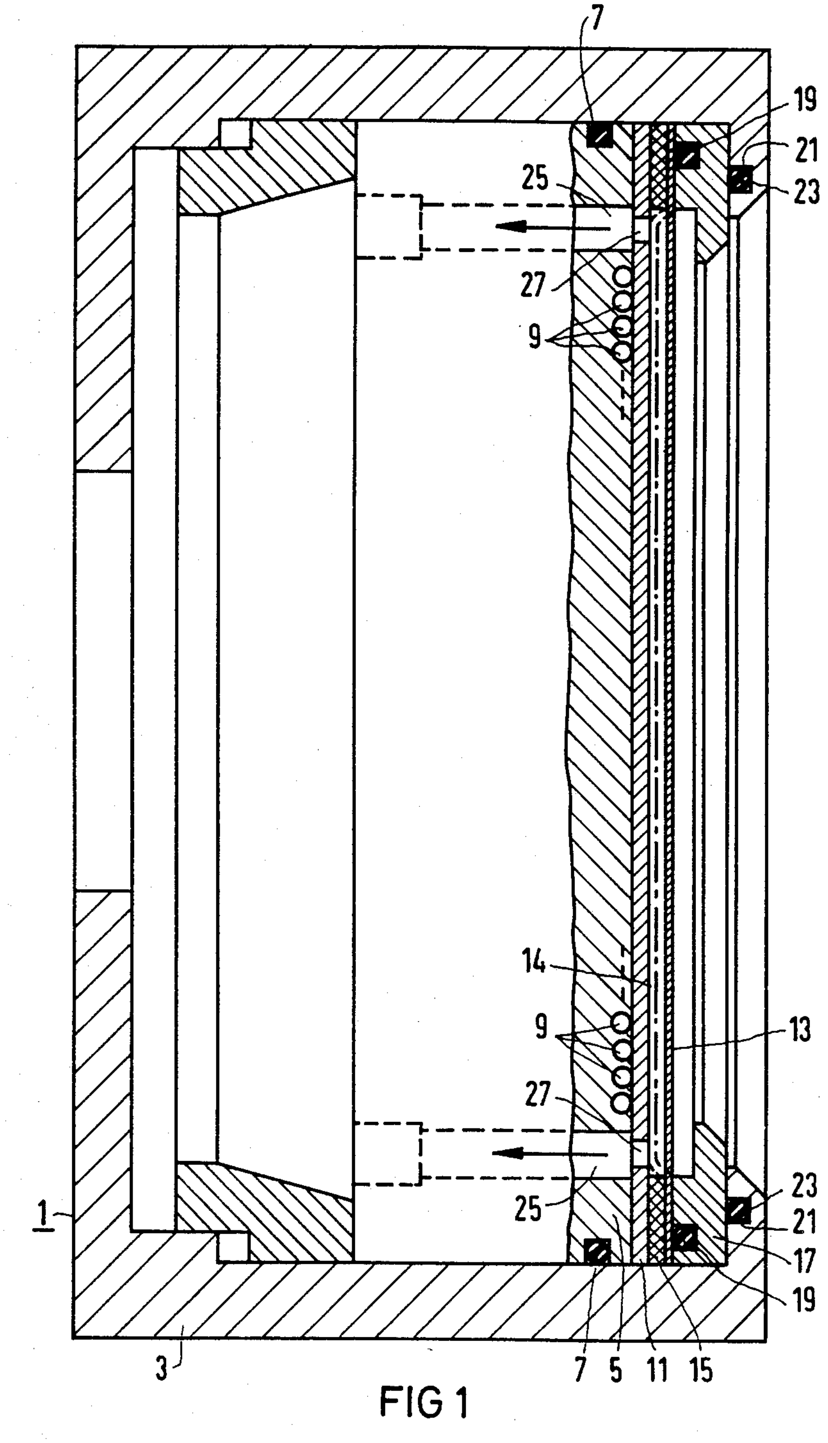
FIG. 1 shows a preferred embodiment of the invention.

In FIG. 1, 1 denotes a shock wave tube. The shock wave tube 1 comprises a cylindrical housing 3, in the region of whose end face, on the inside, a circular coil support 5 is secured. The gap between the coil support 5 and the housing 3 is sealed by means of a first O-ring 7. On the forward side of the coil support 5, a planar single-layer flat coil 9 is fused in. The flat coil 9 is wound in spiral, so that in the center and at the edge there is a connection or terminal for applying a voltage. In front of the fused-in flat coil 9 a circular insulating foil 11 is disposed, which has the same cross-section as the housing 3 of the shock wave tube 1. In front of diaphragm 13 a contoured holding ring 17 is arranged. In a peripheral annular groove of the holding ring 17 is a second O-ring 19. This seals the underside of the holding ring 17 against the diaphragm 13.

Following the holding ring 17, the housing 3 is bent inwardly at right angles, so that an abutment for the holding ring 17 is formed. The inside of this abutment or bent part of the housing 3, is an annular groove 21, which serves to receive a third O-ring 23. By this O-ring 23 the surface of the holding ring 17 is tightly scaled against the housing 3.

In its edge region the coil support 5 is provided with a bore or opening 25, which passes entirely through it, parallel to the main axis. The channel type opening 25 could alternatively also extend on the inside of the housing 3. The insulating foil 11 located at one end of the channel type opening 25 is provided with a hole 27. At the other end of opening 25, a vacuum pump (not shown in FIG. 1) is connected through a pipe (not shown).

When the vacuum pump is turned on, air is withdrawn through bore 25 and hole 27 from the gap 14 which lies between the insulating foil 11 and the diaphragm 13. Diaphragm 13 then moves into the flexed position shown in dash-dot lines. Due to the suction force the diaphragm then lies closely against the insulting foil 11 and hence indirectly against the flat coil 9. If by means of a capacitor 35 (shown in FIG. 2) a steep, high voltage pulse is applied to the flat coil 9, the diaphragm 13 is, due to the resulting strong electromagnetic forces, repelled from the flat coil 9 and from the insulating foil 11. After the voltage pulse, the diaphragm 13 is brought back into position on the insulating foil 11 due to the negative pressure.

The volume between diaphragm 13 and insulating foil 11 is very small as compared with the volume of bore 25 and the feed line to the vacuum pump. It has been found that if the seal is good, the shock wave tube 1 can operate with the negative pressure once created for several hours without having to turn the vacuum pump on again.

In a working unit, the axial length of the shock wave tube 1 was about 10 cm, the inside diameter of the housing 3 about 15 cm, the thickness of the diaphragm 13 about 0.2 mm, the thickness of the spacing ring 15 about 0.2 mm, and the diameter of the bore 25 about 2 mm. The pressure maintained in the air gap 14 was less than 50 mbars (50 hectopascals).

Figure 2:
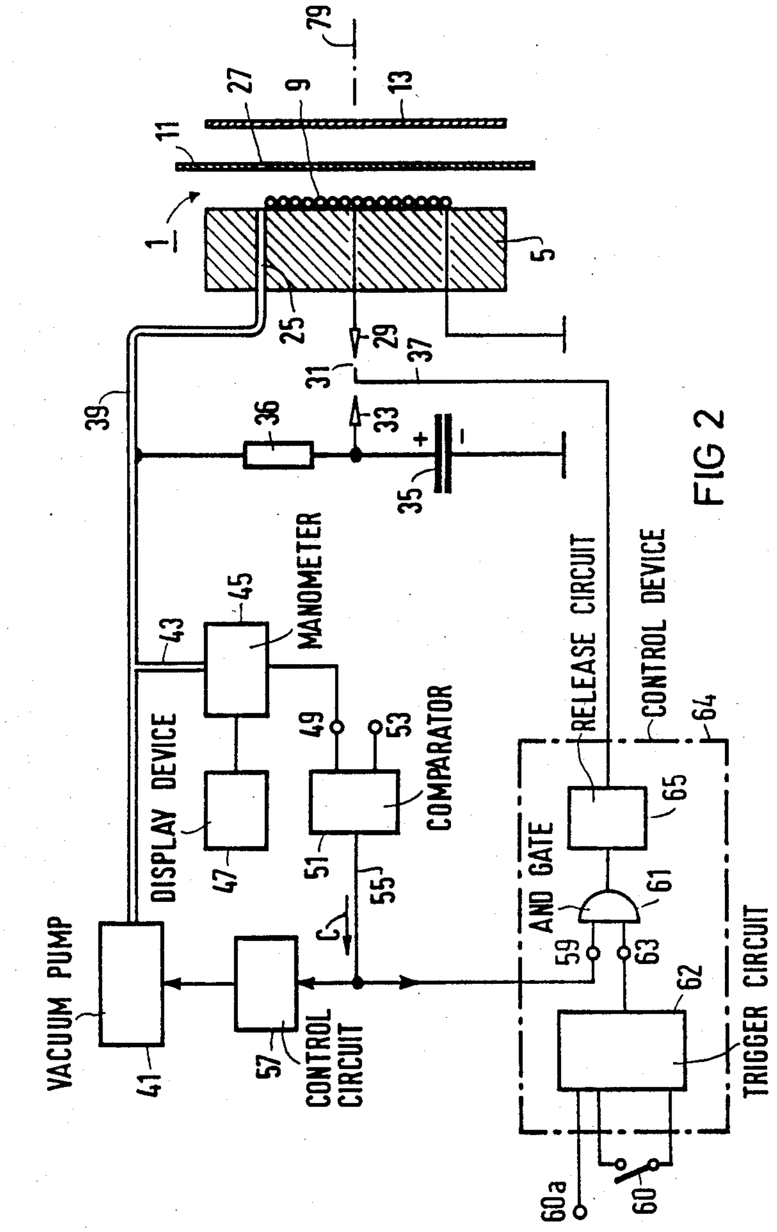
FIG. 2 shows a system which includes the preferred embodiment of FIG. 1.

In FIG. 2 is shown once more the shock wave tube 1 with the housing 3, the coil support 5, the flat coil 9, the insulating foil 11 and the diaphragm 13. The first electric connection or terminal of the flat coil 9, located in its center, is brought out and connected to the first electrode 29 of a spark gap 31. To the second electrode 33 of the spark gap 31 is connected the ungrounded terminal of a grounded capacitor 35. Capacitor 35 is charged by a charging device (not shown) via a series resistance 36. The charging voltage is about 20 kV. Between the first electrode 29 and the second electrode 33 of the spark gap 31 is an auxiliary electrode 37, through which a spark across the spark gap 31 can be initiated. In case of ignition the capacitor 35 discharges abruptly via the flat coil 9, whereupon the metal diaphragm 13 is repelled from the flat coil 9 due to the electromagnetic interaction.

The bore 25 is here a part of a tubular connection which contains also a flexible tube 39 leading to the suction side of a vacuum pump 41. Tube 39 has a branch 43, from which a tap line leads to a pressure measuring device or manometer 45. Connected to the manometer 45 is a display device 47 for display of the negative pressure. The manometer 45 is designed so that it delivers on the output side an electrical signal which is a measure of the negative pressure in the gap 14. It is connected at the output side via a line to the first input 49 of a comparator 51. At the send input 53 of the comparator 51 a voltage is applied which corresponds to an upper limit value for the pressure between the insulating foil 11 and diaphragm 13. This limit value, which may be e.g. 100 mbars, is compared with the measured actual pressure value of manometer 45, and the result of the comparison is delivered at the output 55 of comparator 51 as an electrical output signal C. The output signal C of comparator 51 is supplied to a control circuit 57 for the vacuum pump 41. The vacuum pump 41 is turned on and off via the control circuit 57. It is turned on when said upper limit value is exceeded. The output signal C of comparator 51 is also applied to the first input 59 of an AND gate 61. This gate is blocked when the upper limit value is exceeded. To the second input 63 of the AND gate 61 a trigger signal is applied. It is supplied by a trigger circuit 62. The trigger signal can be generated for example manually via a switch 60. With the closing of switch 60, therefore, a single trigger pulse for example can be released. Alternatively, a sequence of trigger pulses may be released thereby, or there may be released thereby a sequence of trigger pulses with preselectable time interval which determines the succession of shock waves. Moreover the trigger signal may be derived from an apparatus for monitoring the cardiac activity and/or an apparatus for monitoring the respiration. Such an apparatus would then be connected with the trigger circuit 62 via the input 60*a*. The output of the AND gate 61 goes to a release device 65 which operates the ignition or auxiliary electrode 37. Thus the AND gate 61, the trigger circuit 62 and the release circuit 65 together form the part 64 of a control device for the shock wave tube 1. The latter is ignited only when the pressure in the gap 14 is below the limit value.

It is desired to generate shock waves only under appropriate conditions. These conditions are the presence of a sufficient negative pressure in the air gap 14 and the presence of a trigger signal from a connected trigger signal generator 62. The AND gate 61 may have more than two inputs, in order to take into consideration still other release criteria for the shock wave. Hence, patient-related as well as apparatus-related prerequisites can be established.

Figure 3:
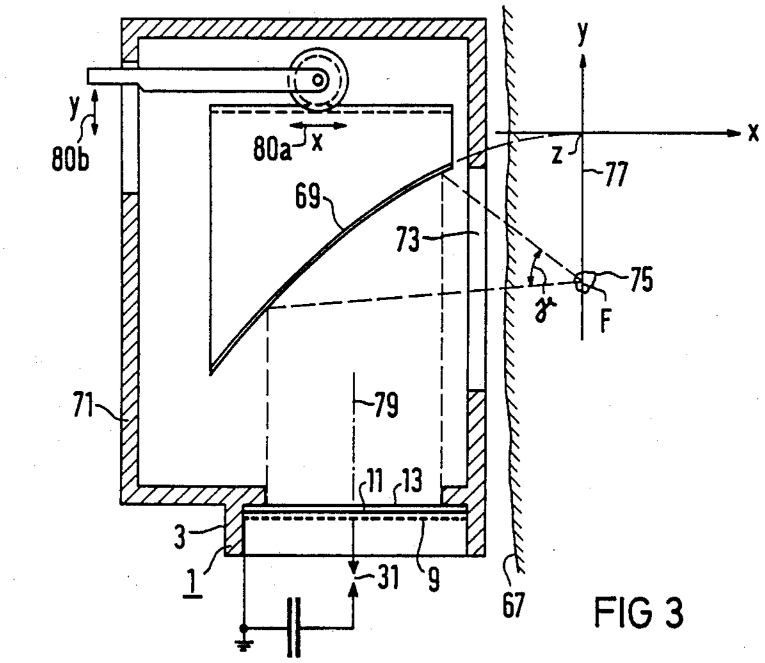
FIG. 3 illustrates a first reflector arrangement for focusing the emitted plane shock wave.
Figure 4:
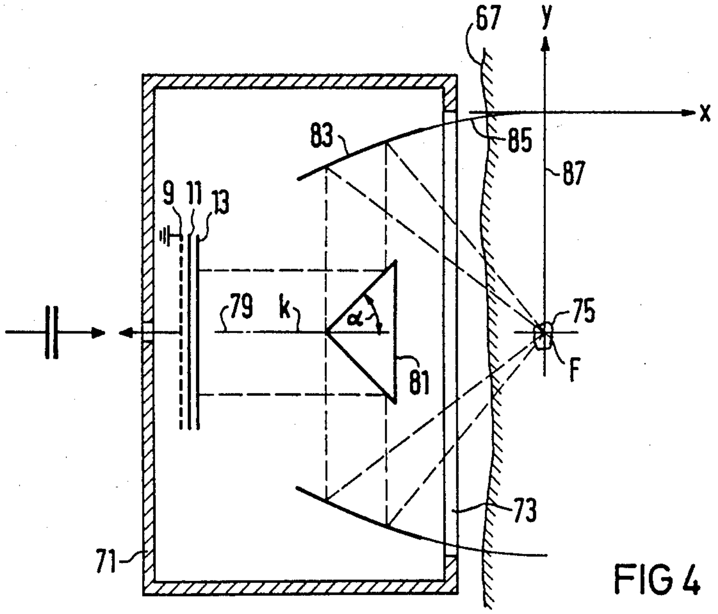
FIG. 4 illustrates a second reflector arrangement for focusing the emitted plane shock wave.

In each of the FIGS. 3 to 7, a planar shock wave tube 1 is shown schematically, namely with the diaphragm 13 and the flat coil 9. In FIGS. 3 and 4 also the spark gap 31 is shown. Beyond the diaphragm 13, the housing 3 continues further.

In FIG. 3, the shock wave tube 1 is oriented substantially parallel to the body surface 67 of a patient. The emitted shock wave strikes a parabolically curved reflector 69, which is arranged opposite the diaphragm 13 on the output side. The parabolic axes are designated by x and y. The shock wave tube 1 and the reflector 69 are here contained in a common apparatus housing 71. Laterlly, at the level of the reflector 69, the apparatus housing 71 has a coupling layer 73. The coupling layer 73 consists for example of EPDM rubber or other material having a low modulus of shear. Such materials are known by themselves in ultrasonic technology. Internally the apparatus housing 71 is filled with water at least between the reflector 69 and diaphragm 13. The coupling layer 73 (preferably a gel) is applied to the body surface 67 of the patient. The patient is oriented so that a concrement 75 inside him, which is to be destroyed, is at the focus F of the parabolic reflector 69. The parabola which determines the curvature of the reflector 69 has an axis of symmetry 77 extending parallel to the main axis 79 of the shock wave tube 1.

The reflector 69 can be displaced parallel to the x- as well as parallel to the y-direction, i.e. perpendicular to or parallel to the direction of shock wave propagation. The directions of mechanical adjustment are indicated by double arrows 80*a*, 80*b*. Moreover the reflector 69 is displaceable also normal thereto, that is, in z-direction. The advantage of this is that a variation of the focus position is possible without displacing the apparatus housing 71 with coupling layer 73 or the patient.

If the diaphragm 13 is deflected due to a voltage pulse, a planar shock wave propagates in the direction of the reflector 69. Thence it is deflected to the side by approximately 90°. The shock wave penetrates through the coupling layer 73 into the patient and converges in the focus F of reflector 69. This is the location of the concrement 75, e.g. a kidney stone, which is fragmented by the shock wave.

An advantage of the shown arrangement is that a relatively large angle of incidence is used with the use of only one reflecting surface.

In FIG. 4 there is opposite the diaphragm 13 a cone 81 whose tip faces toward the diaphragm 13. In this arrangement the cone 81 serves as a first reflector for the planar shock wave and is advantageously made of brass. The plane generatrix of cone 81 has an inclination of 45° relative to the main axis 79 of the shock wave tube 1. The cone axis K and the main axis 79 here have the same direction. Thus the plane shock wave, which due to the circular diaphragm 13 has also a circular cross-section, is transformed at cone 81 into a cylindrical wave perpendicular thereto, which runs outwardly. At the level of cone 81, the latter is surrounded by a second reflector 83, which focuses the shock wave running perpendicularly toward the outside in a focus F. The shape of the second reflector 83, which extends annularly around cone 81, is generated by the rotation of an arc of a parabola 85 (coordinates x, y). The parabola 85 is placed so that its main axis 87 is perpendicular to the axis 79 of the shock wave tube 1. The concrement 75 is located at the focus F of the parabolic ring 83. Here, too, the arrangement consisting of the shock wave tube 1 with the respective reflections 81 and 83 is accommodated in a common apparatus housing 71. The path traversed by the shock wave is filled with water. At the end face on the apparatus housing 71 is again a coupling layer 73, to place the apparatus on the body surface 67 of the patient. An advantage of this arrangement is that the shock wave is coupled into the patient's body with an expecially large aperture. As the second reflector 83 is rotationally symmetrical about the axis 79 of the shock wave tube 1, the foucs F lies on this axis 79. It is thus easy to aim the arrangement at the concrement 75 in the patient. Moreover, an especially compact design results. A shock wave tube 1 with a relatively small diameter, e.g. of five centimeters, can be used here.

Figure 5:
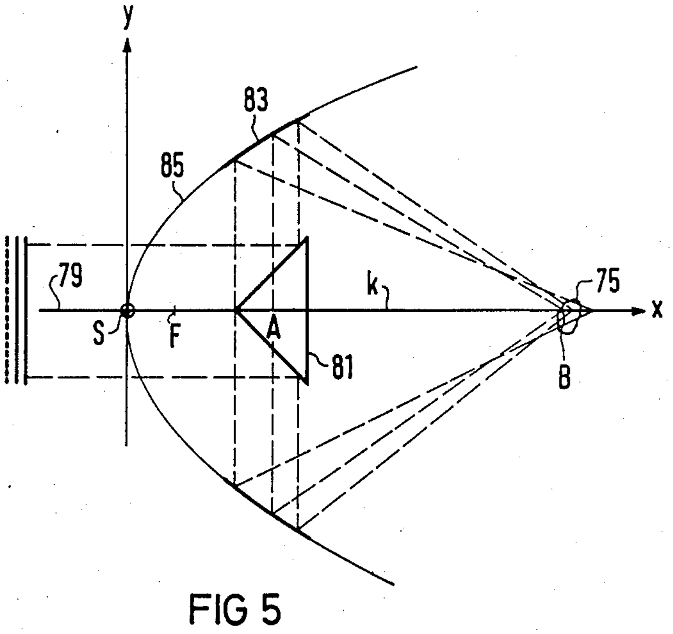
FIG. 5 illustrates a third reflector arrangement for focusing the emitted plane shock wave.

FIG. 5 illustrates an arrangement with a shock wave tube 1 where the shock wave again impinges axially on a cone 81 and is reflected outwardly at right angles, so that a cylindrical shock wave results. Here, too, a second reflector 83 is provided, arranged as a ring around cone 81. The shape of the second reflector 83 has come about here by rotation of the arc of a parabola 85 around the axis 79 of the shock wave tube 1. Unlike the arrangement of FIG. 4, however, the parabolic axis x, which is correlated with the arc and which belongs to the circular ring of the second reflector 83, coincides with the axis 79 of the shock wave tube 1 and with the axis k of cone 81. The geometry of the arrangement is here fixed. The center A of cone 81 has three times the distance from the summit S of parabola 85 as the focus F has from the summit S. The arrangement is aimed at the patient in such a way that the patient's concrement 75 is located on the common axis 79, k of tube 1 and cone 81. A focus zone forms whose summit-nearest point B has nine times the distance from the summit S as does the focus F. This is where the concrement 75 is positioned.

Figure 6:
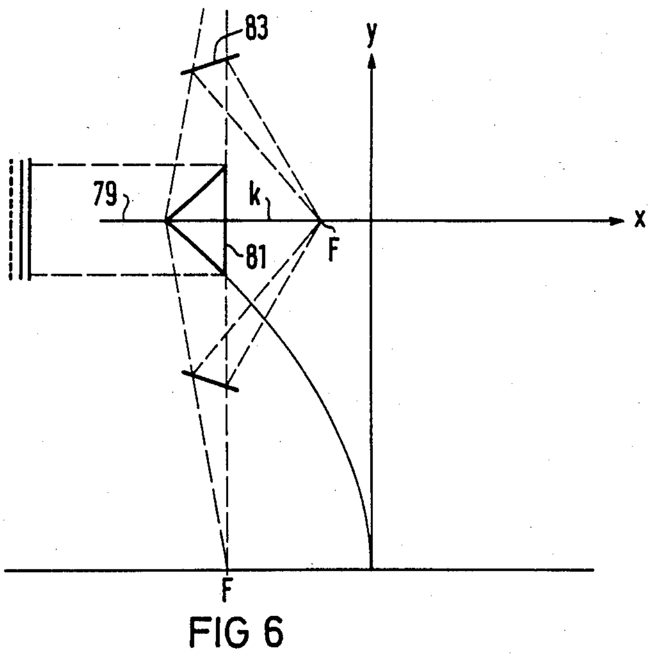
FIG. 6 illustrates a fourth reflector arrangement for focusing the emitted plane shock wave.

FIG. 6 shows another preferred embodiment. There the plane shock wave impinges on a cone 81 whose concave generated surface has come about by rotation of an arc of a parabola about the cone axis k. At the level of cone 81 the latter is surrounded by a second reflector 83 which is formed by rotation of a straight line about the axis k of cone 81. Thence the sound wave is focused on focus F.

Still other favorable reflector systems can be found, by means of which the shock wave can be concentrated. In all reflector arrangements, there is an advantage from elimination of an exit window for the positive pressure space; few interfaces interact with the shock wave and large apertures can be obtained.

Figure 7:
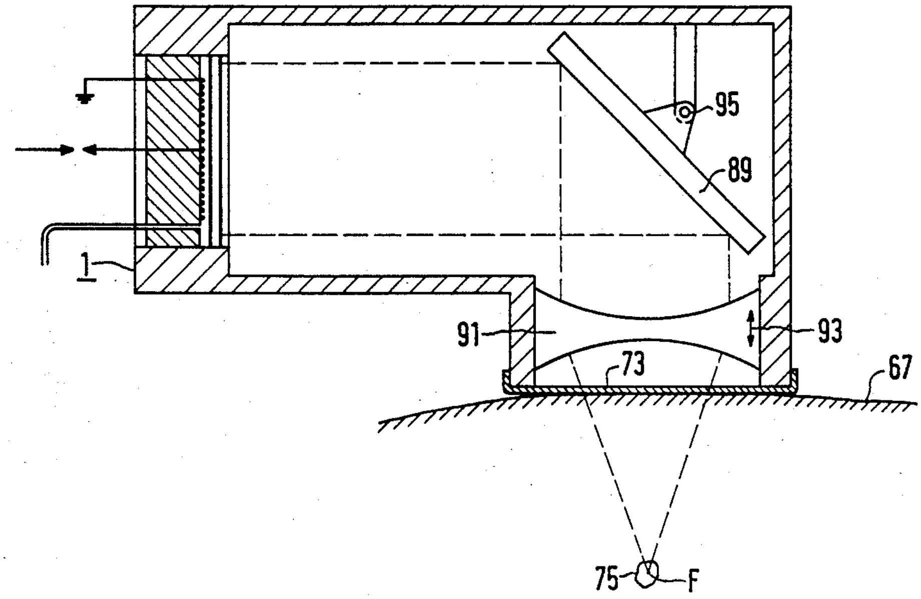
FIG. 7 illustrates a lens system for focusing the emitted plane shock wave.

According to FIG. 7, the shock wave tube 1 is provided with a lens system. The latter comprises a plane reflector 89, arranged in normal position at an angle of 45° to the direction of propagation of the shock waves, and a converging lens 91, onto which the shock waves are directed from the reflector 89. In principle, the arrangement of converging lenses and reflector 89 may be interchanged. Also, the reflector 89 may have a curved surface. For depth adjustment a displacement device for the collecting lens 91 is provided. Its operation is marked by the double arrow 93. The reflector 89 can be tilted by means of a ball joint 95. Thus adjustment of the focus perpendicular to the direction of propagation is possible. The collecting lens 91 is exposed to hardly any wear here.

Those skilled in the art will understand that changes can be made in the preferred embodiments here described, and that these embodiments can be used for other purposes. Such changes and uses are within the scope of the invention, which is limited only by the claims which follow.

What is claimed is:

1. A shock wave tube for fragmenting concrements by production of shock waves, comprising:

a coil;

a diaphragm located adjacent the coil and producing a shock wave when the coil is energized as a result of electromagnetic interaction therewith;

a housing mounted to the coil and diaphragm in a manner that a sealed chamber is bounded thereby; and means for connecting said chamber with a low pressure source, whereby said diaphragm may be drawn towards said coil upon said connection.

2. The shock wave tube of claim 1, wherein the coil is flat and mounted to an end face of an electrically insulating support.

3. The shock wave file of claim 2, wherein a passageway for connecting said chamber to said source passes through said support.

4. The shock wave tube of claim 3, wherein said passageway opens to said chamber as an annular groove which surrounds said coil.

5. The shock wave tube of claim 1, further comprising a pressure measuring device operatively connected to measure the pressure in said chamber.

6. The shock wave tube of claim 5, further comprising means for preventing current from passing through said coil when said pressure exceeds a predetermined maximum value.

7. The shock wave tube of claim 6, wherein said preventing means includes second means for preventing current from passing through said coil in dependence upon a bodily function of a patient.

8. The shock wave tube of claim 7, wherein said bodily function includes cardiac activity.

9. The shock wave tube of claim 7, wherein said bodily function includes respiration.

10. The shock wave tube of claim 5, further comprising means for controlling a low pressure source in such a manner as to maintain said pressure below a predetermined maximum value.

11. The shock wave tube of claim 1, wherein the coil is flat, and wherein the shock wave tube further comprises a reflector system.

12. The shock wave tube of claim 11, wherein the reflector system includes a conical reflector and an annular parabolic reflector surrounding said conical reflector and being coaxial therewith.

13. The shock wave tube of claim 12, wherein a parabola which is the generatrix of the parabolic reflector has a focal length which is one-ninth of a focal length of the reflector system.

14. The shock wave tube of claim 11, wherein the reflector system includes a conical reflector with a parabolic surface and an annular reflector with a surface generated by a straight line, the reflectors being coaxial.

15. The shock wave tube of claim 11, wherein the reflector system includes a parabolic reflector having a surface which is generated by rotation about an axis which is parallel to the tube axis.

16. The shock wave tube of claim 11, wherein the reflector system is movable with respect to the shock wave tube.

17. The shock wave tube of claim 16, wherein the reflector is movable parallel to the shock tube axis.

18. The shock wave tube of claim 16, wherein the reflector is movable perpendicular to the shock tube axis.

19. The shock wave tube of claim 16, wherein the reflector is rotatable with respect to the shock wave tube.

20. The shock wave tube of claim 11, wherein the reflector system is of brass.

21. The shock wave tube of claim 11, wherein the shock wave tube and reflector system are contained in a common housing.

22. The shock wave tube of claim 1, further including an ultrasonic lens system.

23. The shock wave tube of claim 22, wherein the lens system includes a converging lens.

24. The shock wave tube of claim 1, further comprising a reflector system and a converging lens.

25. The shock wave tube of claim 24, wherein the converging lens is movable.

26. The shock wave tube of claim 25, wherein the reflector system is movable.

* * * * *